United States Patent [19]

Balogh

[11] 4,401,838

[45] Aug. 30, 1983

[54] PURIFICATION OF HYDROCARBONS BY TREATMENT WITH POLYAMINES

[75] Inventor: George F. Balogh, North Canton, Ohio

[73] Assignee: The Goodyear Tire & Rubber Company, Akron, Ohio

[21] Appl. No.: 210,931

[22] Filed: Nov. 28, 1980

[51] Int. Cl.[3] .......................... C07C 7/10; C07C 7/11; C10G 21/20
[52] U.S. Cl. .................................... 585/860; 585/836; 208/236
[58] Field of Search ................. 208/236; 585/836, 860

[56] References Cited

U.S. PATENT DOCUMENTS

| | | | |
|---|---|---|---|
| 2,045,057 | 6/1936 | Schulze | 208/236 |
| 2,238,201 | 4/1941 | Wilson et al. | 208/236 |
| 2,418,047 | 3/1947 | Parkes et al. | 208/236 |

FOREIGN PATENT DOCUMENTS

| | | | |
|---|---|---|---|
| 449982 | 7/1948 | Canada | 208/236 |
| 757510 | 8/1980 | U.S.S.R. | 208/236 |

OTHER PUBLICATIONS

Noller, *Chemistry of Organic Compounds*, 1965.

Primary Examiner—Delbert E. Gantz
Assistant Examiner—O. Chaudhuri
Attorney, Agent, or Firm—J. Y. Clowney

[57] ABSTRACT

Isoprene and butadiene are purified by treating a petroleum refinery $C_4$ stream or petroleum refinery $C_5$ stream which contain butadiene or isoprene or relatively pure butadiene or isoprene and carbon disulfide by treatment of these streams with from about 1 to about 7 equivalents of a polyamine. The polyamine reacts with the $CS_2$ impurity to form the dithiocarbamate salt. The hydrocarbon is then separated from the dithiocarbamate salt and any excess unreacted polyamine by water washing this stream or by flash distilling of the hydrocarbon.

11 Claims, No Drawings

PURIFICATION OF HYDROCARBONS BY TREATMENT WITH POLYAMINES

FIELD OF THE INVENTION

This invention relates to the purification of hydrocarbon streams, particularly the removal of carbon disulfide ($CS_2$).

BACKGROUND OF THE INVENTION

Isoprene and butadiene are normally obtained from $C_4$-$C_5$ streams from petroleum refining. In addition to isoprene and butadiene, these streams contain other compounds such as acetylenes, cyclopentadienes and $CS_2$. The acetylenes and cyclopentadienes can only be tolerated to a limited extent in the polymerization of isoprene and butadiene and must be reduced to low levels or removed. On the other hand, $CS_2$ at the expected concentrations, does not interfere with the polymerization process. In fact, some $CS_2$ is beneficial to the polymerization process.

However, one of the methods normally used to remove acetylenes from these streams is by selective hydrogenation. The presence of $CS_2$ poisons the catalyst used for the hydrogenation and, thus, excessive amounts of the expensive catalysts are needed. Another method for removal of the acetylenes and cyclopentadiene is by the use of nickel octoate in conjunction with aluminum alkyls. In this process the $CS_2$ interferes by reacting with the nickel octoate necessitating the use of excessive amounts.

This invention relates to the removal of $CS_2$ in the purification of hydrocarbons.

After the $CS_2$ is removed, the acetylenes and cyclopentadienes can then be readily removed by the methods previously described.

Various methods have been used to remove $CS_2$ from solutions such as oxidations, reductions, reactions with alkaline hydroxides and reaction with alcohols in the presence of alkaline hydroxides to form xanthates. All these methods are impractical when used with $C_4$-$C_5$ hydrocarbon streams, since the residual $CS_2$ interferes with subsequent reactions required to remove the other polymerization inhibitors.

British Pat. No. 570,294 describes a method for removal of $CS_2$ from crude benzene, forerunnings, oils and hydrocarbon vapors using amines. The separation and recovery of the amine and the $CS_2$ follows. The process includes bringing into contact hydrocarbon as a liquid or vapor containing $CS_2$ and a primary $CS_2$ and a primary or secondary amine or a liquid containing such an amine in the presence of ammonia to form ammonium mono or diaryl or alkyl dithiocarbamate removing the dithiocarbamate and decomposing it to regenerate the $CS_2$ and the amine.

British Pat. No. 617,969 describes a process for the removal of $CS_2$ from hydrocarbons by forming a salt of a substituted dithiocarbamic acid. The $CS_2$ is caused to react with a primary amine of a cyclic paraffin in the presence of a strong base in an aqueous solution. The solution of the salt is then separated from the hydrocarbon layer.

In both of these cases, the initial amount of $CS_2$ is quite high (13 g/l). The residual amount of $CS_2$ after treatment can be as high as 400 ppm and in the optimum case is reduced only to 70 ppm. The amine was used in only slightly more than molar amounts relative to the $CS_2$. In addition, excessive amounts of alkali must be used to solubilize the dithiocarbamic acids so that they can be removed by washing with water. The residual $CS_2$ content was excessive to the extent that additional amounts of catalyst would be used up in the subsequent catalytic hydrogenation or other treatment to remove the acetylenes and cyclopentadienes.

SUMMARY OF THE INVENTION

The present invention provides an improved method for the removal of practically all of the $CS_2$ present in the $C_4$-$C_5$ streams containing butadiene, isoprene, acetylenes, cyclopentadienes and $CS_2$. The purified streams can then be selectively hydrogenated and/or treated with other materials to remove the acetylenes and cyclopentadienes and give a mixture of hydrocarbons containing polymer grade butadiene or isoprene.

According to this invention, the $CS_2$ content in $C_4$-$C_5$ hydrocarbons or mixtures thereof can be reduced to negligible amounts by treating the stream with a polyamine of the general formula:

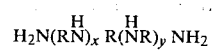

wherein R can be:

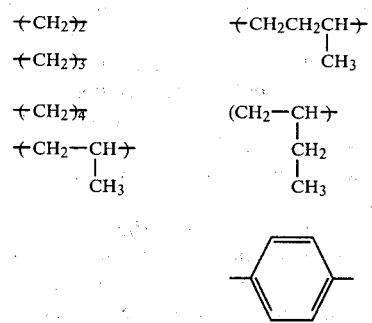

wherein x=0, 1, 2, 3, 4, 5 and y=0, 1, 2, 3, 4, 5 and wherein x and y cannot, at the same time, be 0.

Representative but not limiting of the polyamines that respond to the formula set forth in this statement of invention are tetraethylene pentamine, triethylene tetramine, diethylene diamine or 2-azapentane-1,5-diamine, 4,8-diazadecane-1,10-diamine, pentaethylene hexamine, 4,8,11,15-tetraazaoctadecane-1,18-diamine, dipropylene triamine, 5,8-diazaundecane-1,11-diamine, 3,6-diaza-2,5,8-trimethyloctane-1,8-diamine, 3-azahexane-1,6-diamine, 4,7-diazadecane-1,10-diamine, 1,14-diamino-4,8,11-triazatetradecene, 1,18-diamino-4,8,11,15-triazaoctodecane, pentapropylene hexamine, and other polyamines responding to said formula.

The hydrocarbon stream, which can be either an impure stream containing 4 carbon atom hydrocarbons containing such things as butadiene, butenes, butanes, C-4 acetylenes and carbon disulfide or it can be relatively pure butadiene containing impurities such as carbon disulfide or a $C_5$ hydrocarbon stream containing such things as isoprene, pentane, pentenes, $C_5$ acetylenes, cyclopentadienes and $CS_2$ or it can be relatively pure isoprene containing carbon disulfide after being reacted with the polyamine can be separated from the product of the reaction between the polyamine and the $CS_2$ by either flash distillation or by washing the hydrocarbons with water. The reaction product is a dithiocarbamate salt or a xanthate which is soluble in water. The resultant hydrocarbon stream, whether it be an impure $C_4$ or $C_5$ stream containing other things such as acetylenes and other saturated or unsaturated $C_4$ hydrocarbons or a $C_5$ stream containing isoprene, pentene, pentane, $C_5$ acetylenes and cyclopentadienes, or whether it is relatively pure butadiene or a relatively pure isoprene which still contains acetylenes can be readily hydrogenated to eliminate acetylenes and, in the case of $C_5$ streams, cyclopentadiene using a minimum amount of a hydrogenation catalyst.

In the practice of this invention, the hydrocarbon stream, whether it be relatively pure butadiene or relatively pure isoprene or a relatively impure $C_4$ or $C_5$ hydrocarbon stream or a mixed $C_4$, $C_5$ stream containing carbon disulfide for treatment with about 1 to about 7 or more molar equivalents of the polyamine relative to the amount of carbon disulfide contained in the hydrocarbon. For example, when a $C_5$ stream containing about 400 parts per million (ppm) of $CS_2$ was treated with about two molar equivalents, tetraethylene pentamine and allowed to be mixed and stand for twenty minutes and the hydrocarbon flash distilled, the $CS_2$ content was analyzed and determined to be less than 10 ppm.

It has been determined that about one mole equivalent of a polyamine relative to the amount of carbon disulfide is a practical lower limit. There is no upper limit, however, it has been determined that about 7 molar equivalents of polyamine relative to the carbon disulfide contained in the hydrocarbon is sufficient to remove the carbon disulfide to an acceptable level. Any further increase in the molar ratio of polyamine is thus uneconomical.

It has been determined that the time required to contact the hydrocarbon with the polyamine should probably be at least about 5 minutes. There is no upper limit to the length of the contact time except excessive time beyond much more than one hour does not produce any additional benefit.

The hydrocarbon stream which is being treated with the polyamine of this invention, should not contain excessive water other than the water which is soluble in the hydrocarbon for best results. If excessive water is entrained in the hydrocarbon stream being treated, the contact between the polyamine and the $CS_2$ is not sufficient because the polyamine is soluble in the water and would not be available to react with the $CS_2$ which is soluble in the hydrocarbon. In other words, best results are obtained when the reaction between the polyamine and the hydrocarbon stream containing a one-phase system comprising hydrocarbon and water.

EXAMPLE 1

Several 500 ml. samples of a solution of isoprene (72%) and pentane containing 400 ppm $CS_2$ was treated with 2 molar equivalents of tetraethylene pentamine (TEPA) for each molar equivalent of $CS_2$ in each of the samples. A white slurry of the dithiocarbamate was produced in each sample bottle, after shaking for 20 minutes. Each of the samples was extracted twice with 50 ml. of water for each 500 ml of solution. Each extraction involved 5 minutes of shaking followed by 1 minute for separation of phases. Spectrophotometric analysis of hydrocarbon mixture indicated a range of 3–6 ppm $CS_2$ based on the isoprene contained in each sample.

EXAMPLE 2

An apparatus was prepared for the continuous removal of $CS_2$ via the amine treatment. It consists of a system of metering the separate isoprene/pentane/$CS_2$ and the polyamine streams through a mixer into a reaction tank. The flow rates of the two streams were adjusted to obtain the desired residence times and polyamine/$CS_2$ ratios. The treated hydrocarbon effluent was then washed batchwise to remove unreacted excess polyamine and the $CS_2$/amine by-product.

A mixture of 72/28 weight percent isoprene/pentane was prepared to approximate a commercial isoprene/pentane composition. $CS_2$ was added to obtain a concentration of about 500 ppm as expected in a commercial $C_4$–$C_5$ stream. Water was added to simulate a water saturated condition. An analysis of the mixture is as follows:

| | |
|---|---|
| Isoprene | 70.67% |
| $C_4$'s | 0.15% |
| $C_5$'s other than isoprene | 29.08% |
| $C_6$'s | 0.10% |
| $CS_2$ | 570 ppm |
| $H_2O$ | 164 ppm |

The polyamine used in the reaction was 4,7-diazadecane-1,10-diamine, furnished by BASF Wyandotte Corp as N4 amine and contains a minimum of 96.59 of the compound. Although the polyamine could be used neat, a 15 percent by weight solution in the isoprene/pentane mixture was used in the continuous run.

The two streams, isoprene/pentane azeotrope mixture and the N-4 Amine solution were pressured through a rotometer to the mixer. The isoprene/pentane stream was regulated to flow over a 36–110 ml/min. range and the N-4 Amine solution over a 0.4 to 1.3 ml/min. range. Reaction between the amine and $CS_2$ started rapidly and was visually observed in the glass-walled mixer. The effluent entered a 4 inch glass pipe for reaction residence. Based on previously developed data, a range of 1.25 to 2.05 mole ratio polyamine to $CS_2$ and 60 to 90 minutes residence time were used. The samples were collected and washed with water to remove the dithiocarbamate salt and excess polyamine. The hydrocarbon azeotrope was then analyzed for residual $CS_2$. Table I gives conditions necessary to reduce the $CS_2$ from 570 ppm to less than 10 ppm, and in some cases to 0 ppm of $CS_2$.

TABLE I

| Run No. | Residence Time, min. | Ratio Amine/$CS_2$ | Residual $CS_2$ |
|---|---|---|---|
| 1 | 60 | 2.05 | 0 |
| 2 | 90 | 1.55 | 0 |
| 3 | 75 | 1.80 | <1 |
| 4 | 75 | 1.30 | <1 |
| 5 | 60 | 1.55 | 3 |
| 6 | 90 | 1.25 | 1.8 |

EXAMPLE 3

The following comparative example is submitted to indicate that the polyamines of this invention are much more effective to remove $CS_2$ from a hydrocarbon.

The following amines were tested for their efficiency in removing $CS_2$ in a similar manner as outlined in Example 1 for tetraethylene pentamine: diethylene triamine, morpholine, di-n-butyl amine, ethylene diamine, n-butyl amine, ethanol amine and piperidine. To obtain the relative efficiency of the various amines as compared with tetraethylene pentamine, a 72 percent isoprene/pentane solution containing 444 ppm of $CS_2$ was treated for 20 minutes with 1.34 molar equivalents of amine. After two successive water washes the hydrocarbon solutions were analyzed for residual $CS_2$. The results are shown in Table II.

TABLE II

| Example | Amine | Residual $CS_2$ ppm | % $CS_2$ Removed |
|---|---|---|---|
| 1 | TEPA | 15 | 96.6 |
| 2 | Diethylene triamine | 171 | 61.6 |
| 3 | Piperidine | 227 | 48.9 |
| 4 | n-Butylamine | 322 | 27.6 |
| 5 | Di-n-butylamine | 327 | 26.5 |
| 6 | Ethylene diamine | 356 | 20.0 |
| 7 | Morpholine | 399 | 10.3 |
| 8 | Ethanol amine | 415 | 6.7 |
| 9 | $H_2O$ Wash only | 435 | 2.2 |

On an equimolecular basis TEPA is 10 times as effective as the next compound on the list in removing $CS_2$ from the isoprene/pentane azeotrope. The other materials are even less efficient.

BASF Wyandotte Corp. manufactures a series of polyamines. They are as follows:

N-3 Amine, which is 3-azahexane-1,6-diamine;
N-4 Amine, which is 4,7-diazadecane-1,10-diamine;
N-5 Amine, which is >50 percent 1,14-diamine-4,8,11-triazatetradecane;
N-6 Amine, which is >50 percent 1,18-diamine-4,8,11,15-triazaoctodecane;
$N_3/N_4$ Amine mixture, which is 60 to 70 percent $N_3$ Amine and 30 to 40 percent $N_4$ Amine;
Polypropylene polyamine-6, which is >60 percent pentapropylene hexamine.

These polyamines have been screened for their ability to remove $CS_2$ from isoprene/pentane solutions in comparison with TEPA. In the initial screening 200 ml. aliquots of the isoprene/pentane solution containing 509 ppm $CS_2$ was treated with 0.1 g. of each of the polyamine. The results of these tests are shown in Table III.

TABLE III

| Example | Amine | Residual $CS_2$ ppm |
|---|---|---|
| 1 | N-3 | 1.9 |
| 2 | N-4 | 28.5 |
| 3 | N-5 | 109.5 |
| 4 | N-6 | >143 |
| 5 | TEPA | 127.2 |

At the concentration level of polyamine tested N-3 removes all but 1.9 ppm of the $CS_2$ while TEPA removes all but 127 ppm. With the exception of N-6, each of these polyamines is more efficient than TEPA. On a molar basis they should all reduce the $CS_2$ content to 10 ppm using a 1-3 molar ratio. It is obvious that mixtures of these polyamines with each other or with other amines previously mentioned would give intermediate results.

EXAMPLE 4

A pure isoprene stream of a purity of 99 plus percent was continuously fed at about 24°-27° C. to a 2271 liter reaction tank at the rate of 30.9 kilograms per minute. Tetraethylene pentamine is added to the line feeding the isoprene to the tank, at a rate of 11.2 up to 19.0 mls. per minute. This gives a polyamine/$CS_2$ mole ratio varying from 2.5/1 to 5.9/1. The out-flow from this reaction tank was fed to a counter current water extraction setup where the excess polyamine and the reaction product of the polyamine and the $CS_2$ is washed out of the isoprene. Samples were taken periodically, both of the isoprene feed stream containing $CS_2$ and the treated isoprene after it had been water washed. Typical data for this continuous purification is given below.

| Polyamine Flow Rate | Initial $CS_2$ Level | Final $CS_2$ Level |
|---|---|---|
| 19.0 mls/min. | 42 ppm | 2 |
|  | 47 ppm | 5 |
|  | 82 ppm | 23 |
| 15.1 mls/min. | 53 ppm | 9 |
|  | 63 ppm | 13 |
|  | 63 ppm | 12 |
| 11.2 mls/min. | 59 ppm | 22 |
|  | 48 ppm | 19 |
|  | 57 ppm | 20 |

While certain representative embodiments and details have been shown for the purpose of illustrating the invention, it will be apparent to those skilled in this art that various changes and modifications may be made therein without departing from the spirit or scope of the invention.

What is claimed is:

1. A process for reducing the amount of carbon-disulfide in a hydrocarbon stream which comprises treating the hydrocarbon stream containing carbon disulfide with a polyamine with the general formula:

$$H_2N(R\overset{H}{N})_x R(\overset{H}{N}R)_y NH_2$$

wherein R can be:

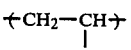

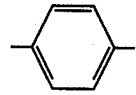

wherein x=0, 1, 2, 3, 4, 5 and y=0, 1, 2, 3, 4, 5 and wherein x and y cannot, at the same time, be 0, to form a reaction product which is a polyamine salt of dithiocarbamate and subsequently separating the product formed by the reaction of the polyamine and the carbon disulfide from the hydrocarbon stream.

2. The process as described in claim 1 wherein the hydrocarbon stream is an isoprene/pentane azeotropic mixture.

3. The process as described in claim 1 wherein the hydrocarbon stream is 99 percent pure isoprene.

4. The process as described in claim 1 wherein the polyamine and carbon disulfide reaction product is removed from the hydrocarbon by washing the hydrocarbon stream containing the said reaction product with water.

5. The process as described in claim 1 wherein the treatment with the polyamine and the separation of the reaction product of the polyamine and carbon disulfide is a continuous process.

6. In a process described in claim 1 in which the polyamine is 3-azahexane-1,6-diamine.

7. In a process described in claim 1 in which the polyamine is 4,7-diazadecane-1,10-diamine.

8. A process according to claim 1 in which more than 50 percent of the polyamine is 1,14-diamine-4,8,11-triazatetradecane.

9. A process according to claim 1 in which more than 50 percent of the polyamine is 1,18-diamine-4,8,11,15-triazaoctodecane.

10. A process according to claim 1 in which the polyamine is 60-to 70 weight percent of 3-azahexane-1,10-diamine.

11. A process according to claim 1 in which the polyamine is more than 60 percent pentapropylene hexamine.

* * * * *

UNITED STATES PATENT OFFICE
CERTIFICATE OF CORRECTION

PATENT NO. : 4,401,838

DATED : August 30, 1983

INVENTOR(S) : George F. Balogh

It is certified that error appears in the above-identified patent and that said Letters Patent are hereby corrected as shown below:

Column 8, line 8, after "3-azahexane-" insert --1,6-diamine and 30 to 40 weight percent of 4,7-diazadecane--.

Signed and Sealed this

Second Day of October 1984

[SEAL]

Attest:

GERALD J. MOSSINGHOFF

Attesting Officer

Commissioner of Patents and Trademarks